US010307305B1

(12) United States Patent
Hodges

(10) Patent No.: US 10,307,305 B1
(45) Date of Patent: Jun. 4, 2019

(54) MALE INCONTINENCE DEVICE

(71) Applicant: Charleen Hodges, Hardeeville, SC (US)

(72) Inventor: Charleen Hodges, Hardeeville, SC (US)

( * ) Notice: Subject to any disclaimer, the term of this patent is extended or adjusted under 35 U.S.C. 154(b) by 509 days.

(21) Appl. No.: 15/162,712

(22) Filed: May 24, 2016

(51) Int. Cl.
*A61F 5/453* (2006.01)
*A61F 5/457* (2006.01)
*A61F 13/471* (2006.01)
*A61F 5/44* (2006.01)

(52) U.S. Cl.
CPC .......... *A61F 13/471* (2013.01); *A61F 5/4408* (2013.01); *A61F 5/453* (2013.01)

(58) Field of Classification Search
CPC ........ A61F 5/44; A61F 5/4401; A61F 5/4408; A61F 5/451; A61F 5/453; A61F 2005/4402; A61F 13/471; A61F 13/4915; A61F 13/64
USPC ..................................... 604/385.09
See application file for complete search history.

(56) References Cited

U.S. PATENT DOCUMENTS

| | | | |
|---|---|---|---|
| 4,601,716 A | 7/1986 | Smith | |
| 4,627,846 A | 12/1986 | Ternstrom | |
| 5,074,853 A | 12/1991 | Bryant | |
| 5,618,279 A * | 4/1997 | Pudlo | A61F 5/40 2/403 |
| 6,197,011 B1 * | 3/2001 | Freitas | A61F 13/471 604/385.03 |
| 7,066,920 B1 * | 6/2006 | Mula | A61F 13/471 604/349 |
| D528,205 S | 9/2006 | Larsen | |
| 8,277,426 B2 | 10/2012 | Wilcox | |
| 8,568,376 B2 * | 10/2013 | Delattre | A61F 13/471 604/385.01 |
| 8,986,271 B1 * | 3/2015 | Horne | A61F 5/4408 604/349 |

FOREIGN PATENT DOCUMENTS

WO    8707136 A1    12/1987

\* cited by examiner

*Primary Examiner* — Catherine L Anderson

(57) ABSTRACT

A male incontinence device is configured to contain urine and/or blood involuntarily expelled from the penis of a wearer. In some implementations, the male incontinence device may be easily donned and removed for disposal. In this way, both ambulatory and non-ambulatory wearers may be fitted with the male incontinence device.

8 Claims, 6 Drawing Sheets

MALE INCONTINENCE DEVICE

CROSS REFERENCES TO RELATED APPLICATIONS

Not Applicable

STATEMENT REGARDING FEDERALLY SPONSORED RESEARCH

Not Applicable

REFERENCE TO APPENDIX

Not Applicable

BACKGROUND OF THE INVENTION

Field of the Invention

Urinary incontinence is a medical condition that can negatively affect quality of life and be very embarrassing for those individuals suffering from the condition. Urinary incontinence is not limited to individuals who are incapacitated and may affect those who are highly active.

Traditional incontinence garments, often referred to as diapers, can be used to absorb urine and blood involuntarily expelled through the penis as the result of urinary incontinence. Unfortunately, these incontinence garments leave the sensitive skin of the scrotum and perineum exposed to contact with urine and blood. Such contact by urine and blood often results in ulceration and skin necrosis and/or secondary infection. Also, traditional incontinence garments can be difficult to remove from an incapacitated wearer. Thus, there is a need for an improved incontinence garment for males.

SUMMARY OF INVENTION

Implementations of male incontinence device are provided. The male incontinence device described herein is configured to contain urine and/or blood involuntarily expelled from the penis of a wearer. In some implementations, the male incontinence device may be easily donned and removed for disposal. In this way, both ambulatory and non-ambulatory wearers may be fitted with the male incontinence device.

In some implementations, the male incontinence device may comprise of a waistband coupled to an absorbent pouch for receiving the penis of a wearer.

In some implementations, the pouch may comprise of a garment-side layer and a body-side layer connected together to form a cavity there between. In some implementations, the body-side layer may include an opening there through. In this way, the penis of a wearer may pass through the body-side layer and into the interior opening of the pouch.

These and other features and advantages of the present invention will become more apparent to one of ordinary skill in the art after a review of the following detailed description, claims, and accompanying drawings.

BRIEF DESCRIPTION OF DRAWINGS

The accompanying drawings, which are included to provide a further understanding of the invention are incorporated in and constitute a part of this specification, illustrate an embodiment of the invention and together with the description serve to explain the principles of the invention. They are meant to be exemplary illustrations provided to enable persons skilled in the art to practice the disclosure and are not intended to limit the scope of the appended claims.

DETAILED DESCRIPTION OF THE EMBODIMENT

The following detailed description is merely exemplary in nature and is not intended to limit the described embodiments of the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to practice the disclosure and are not intended to limit the scope of the appended claims. Furthermore, there is no intention to be bound by any expressed or implied theory presented in the preceding technical field, background, brief summary or the following detailed description.

Detailed reference will now be made to a first potential embodiment of the disclosure, which is illustrated in FIGS. 1 through 5.

Figure 1:
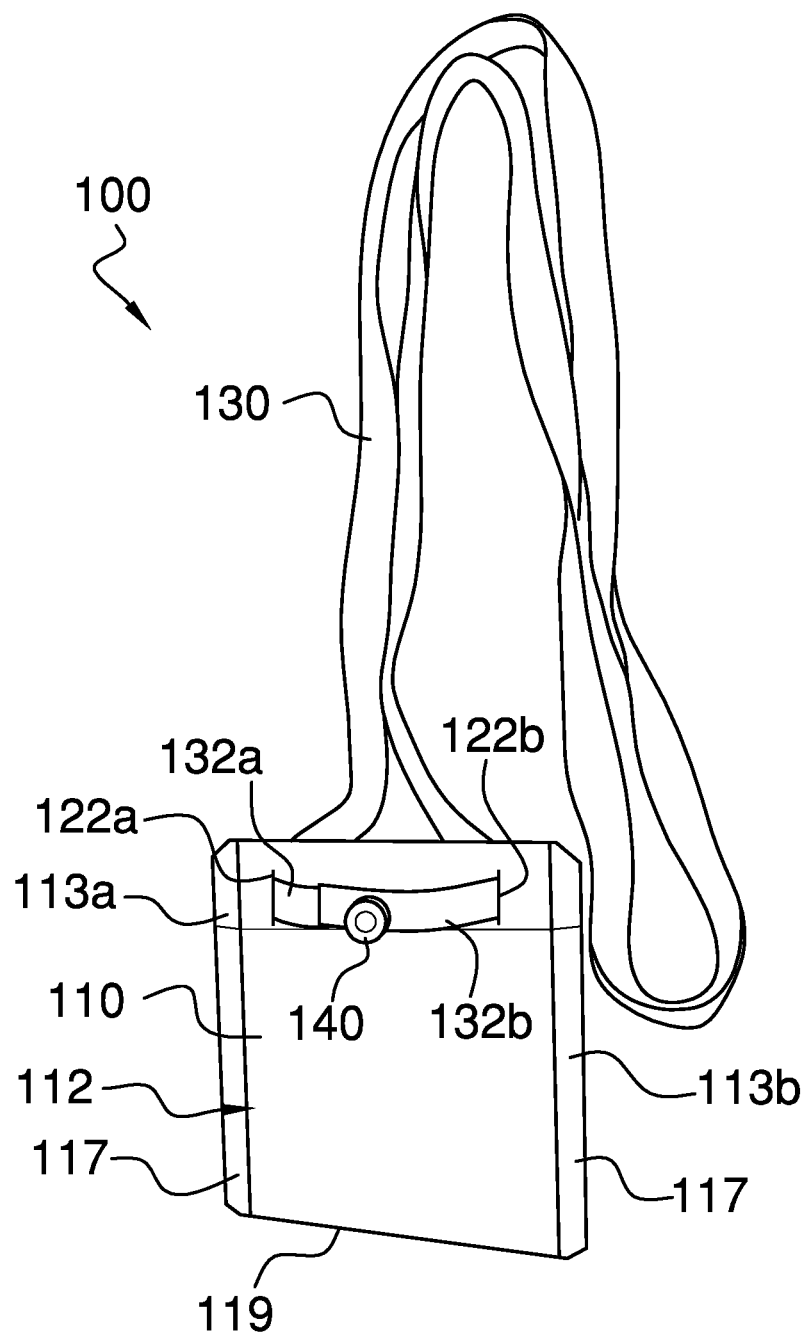
FIG. 1 illustrates a front side view of an example male incontinence device according to the present disclosure.
Figure 2:
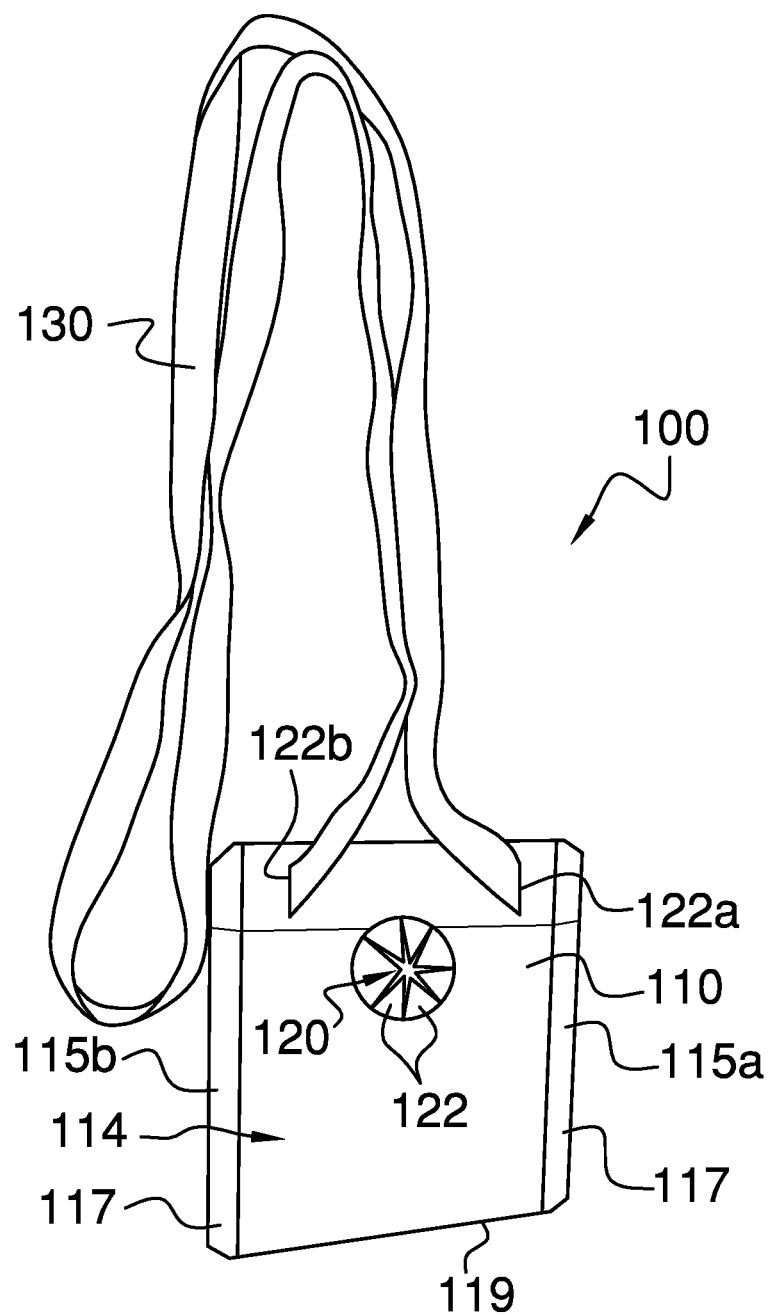
FIG. 2 illustrates a back side view of the male incontinence device shown in FIG. 1.
Figure 3:
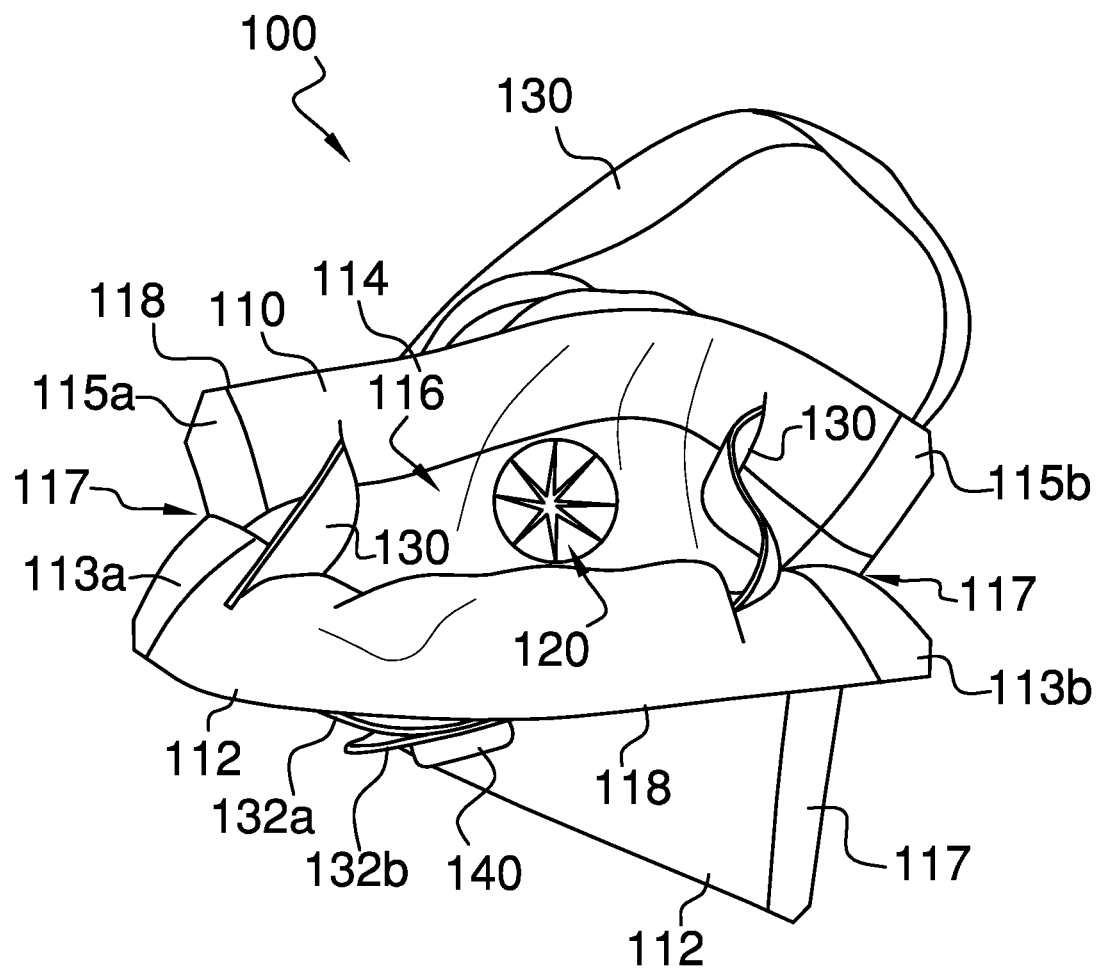
FIG. 3 illustrates a top view of the male incontinence device shown in FIGS. 1 and 2.

FIGS. 1-3 illustrate an example of a male incontinence device 100 according to the present disclosure. Implementations of the male incontinence device 100 described herein are configured to contain urine and/or blood involuntarily expelled from the penis of a wearer. In some implementations, the male incontinence device 100 may be easily donned and removed for disposal. In this way, both ambulatory and nonambulatory wearers may be fitted with the male incontinence device 100. In some implementations, the male incontinence device 100 may be used in combination with an incontinence garment, also referred to as a diaper.

As shown in FIGS. 1-3, in some implementations, the male incontinence device 100 may comprise of a waistband 130 coupled to a pouch 110 adapted for receiving the penis of a wearer. In some implementations, the waistband 130 may be configured to removably secure about the waist of a wearer.

In some implementations, the pouch 110 may comprise a garment-side layer 112 (see, e.g., FIG. 1) and a body-side layer 114 (see, e.g., FIG. 2) connected together to form a cavity 116 there between (see, e.g., FIG. 3). In some implementations, the body-side layer 114 may include an opening 120 there through (see, e.g., FIG. 2). In this way, the penis of a wearer may pass through the body-side layer 114 and into the interior cavity 116 of the pouch 110 during use.

As shown in FIGS. 1 and 2, in some implementations, the pouch 110 may be square shaped. In some implementations, the pouch 110 may be any suitable shape. In some implementations, the garment-side layer 112 and the body-side layer 114 may be separate ends of a single piece of material folded back onto itself to form the pouch 110 (see, e.g., FIG. 1). In this way, the bottom side 119 of the pouch 110 is sealed. In some implementations, the pouch 110 may include a perimeter seal 117 joining at least a first side edge 113a and a second side edge 113b of the garment-side layer 112 to the first side edge 115a and the second side edge 115b of the body-side layer 114, respectively (see, e.g., FIG. 3). Leaving the top side 118 of the pouch 110 unsealed allows a caregiver or wearer to assess the condition of the penis and/or interior cavity 116 without removing the male incontinence device 100 from the wearer. In this way, a caregiver or wearer may more easily tell if the male incontinence device 110 needs to be removed and replace. In some implementations, the perimeter seal 117 may extend continuously proximate the outer perimeter of the garment-side layer 112 and the body-side layer 114 of the pouch 110. A person of ordinary skill in the art having the benefit of the present disclosure would know how to create the perimeter seal 117.

As shown in FIG. 2, in some implementations, the opening 120 through the body-side layer 114 of the pouch 110 is an aperture formed from a plurality of radial slits. In some implementations, the radial slits may be cut to form a plurality of flaps 122 which extend into the interior cavity 116 of the pouch 110 when a penis 500 of a wearer 501 is inserted therein (see, e.g., FIG. 5). In some implementations, the use of radial slits may allow the opening 120 to more comfortably conform to the shaft of said penis 500 passing there through. In this way, the comfort of the male incontinence device 100 may be improved through the use of the radial slits. In some implementations, the opening 120 may be formed to have any suitable shape for use as part of a male incontinence device 100.

In some implementations, the interior side of both the garment-side layer 112 and the body-side layer 114 may absorb moisture (e.g. blood and/or urine). In some implementations, the interior side of the pouch 110 may be an absorbent soft fibrous nonwoven material layer.

In some implementations, the exterior side of both the garment-side layer 112 and the body-side layer 114 may include a moisture impermeable coating and/or layer thereon. In this way, moisture (e.g., blood and/or urine) collected within the pouch 110 may be prevented from leaking there through. In some implementations, the garment-side layer 112 and the body-side layer 114 of the pouch may include a liquid-proof polyethylene coating and/or layer thereon.

In some implementations, the pouch 110 may be manufactured from a polyurethane laminate.

As shown in FIG. 1, some implementations, the waistband 130 may have a first end 132a and a second end 132b. In some implementations, the first end 132a and the second end 132b of the waistband 130 may be secured together through the use of a fastener such as a button 140 (see, e.g., FIG. 1). In some implementations, the first end 132a and the second end 132 of the waistband 130 may be secured together through the use of an adhesive, snaps, buttons, hook-and-loop fasteners (e.g., Velcro), magnets and/or other reclosable fasteners or any other attachment or fastening technology existing or developed in the future to secure the first end 132a and the second end 132b of the waistband 130 together.

As shown in FIGS. 1-3, in some implementations, the waistband 130 may be coupled to an upper portion of the pouch 110 adjacent a top side 118 thereof. In some implementations, a first opening 122a and a second 122b (collectively openings 122) may extend through the garment-side layer 112 and the body-side layer 114 of the pouch 110 (see, e.g., FIGS. 1-2). The openings 122 of the pouch 110 are configured to allow a portion of the waistband 130 to pass there through. In some implementations, a first end 132a and a second end 132b of the waistband 130 may extend through the first opening 122a and the second opening 122b, respectively, of the pouch 110 (see, e.g., FIG. 1). In some implementations, the first opening 122a may be positioned adjacent the first side edge 115a of the body-side layer 114 and the first side edge 113a of the garment-side layer 112 while the second opening 122b may be positioned adjacent to the second side edge 115b of the body-side layer 114 and the second side edge 113b of the garment-side layer 112 (see, e.g., FIGS. 1 and 2). In this way, the waistband 130 does not prevent a caregiver or wearer from opening a top side 118 of the pouch 110 and viewing the interior cavity 116 thereof (see, e.g., FIG. 3). In some implementations, the openings 122 may be positioned at any suitable location on the pouch 110.

In some implementations, the waistband 130 may be removably coupled to the pouch 110 (see, e.g., FIG. 1). In this way, the waistband 130 may be reusable. In some implementations, the waistband 130 may be permanently coupled to the pouch 110. In some implementations, the waistband 130 may be elastic. In some implementations, the length of the waistband 130 may be adjustable. In some implementations, the length of the waistband 130 may not be adjustable.

To secure the male incontinence device 100 in place, in some implementations, the penis of a wearer may be initially inserted through the opening 120 in the body-side layer 114 of the pouch 110. Next, in some implementations, the first end 132a of the waistband 130 may be pulled around the waist of the wearer. Then, in some implementations, the first end 132a of the waistband 130 is inserted into the first opening 122a of the body-side layer 114 and out through the garment-side layer 112 of the pouch 110 (see, e.g., FIG. 1). Next, the first end 132a may be secured to the second end 132b of the waistband 130 (see, e.g., FIG. 1). In this way, the pouch 110 may be supported by the waistband 130.

To remove the male incontinence device 100, in some implementations, the above steps may be performed in reverse order.

Figure 4A:
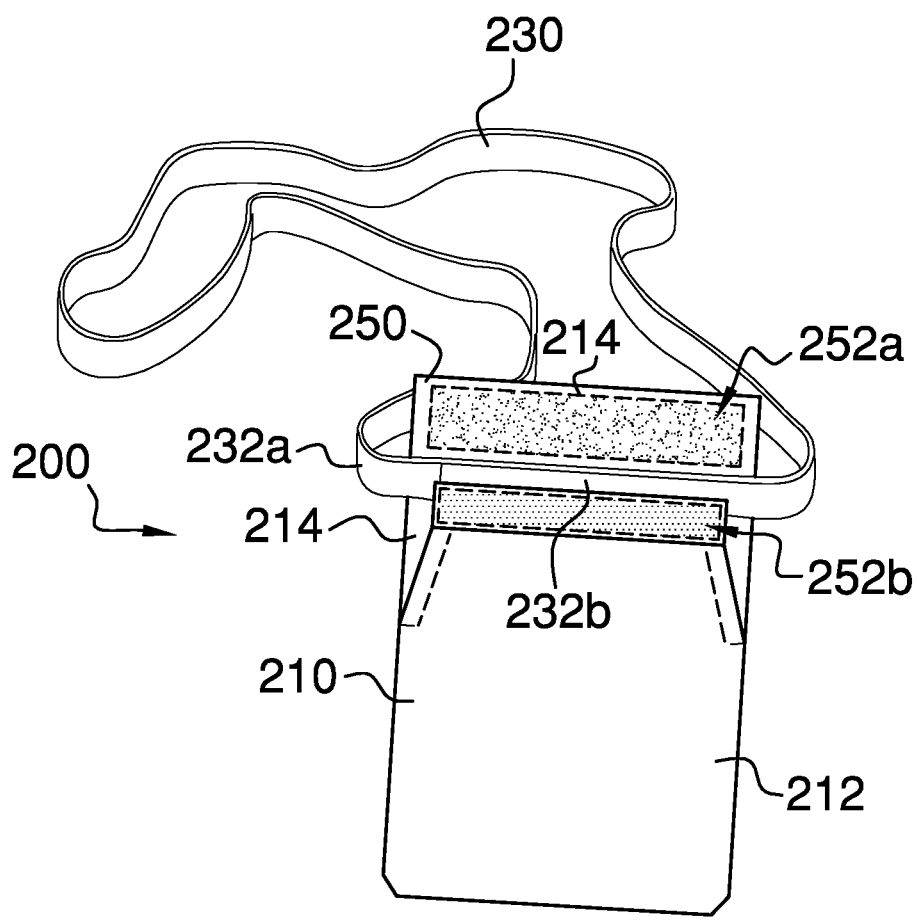
FIGS. 4A and 4B illustrate another example implementation of a male incontinence device.
Figure 4B:
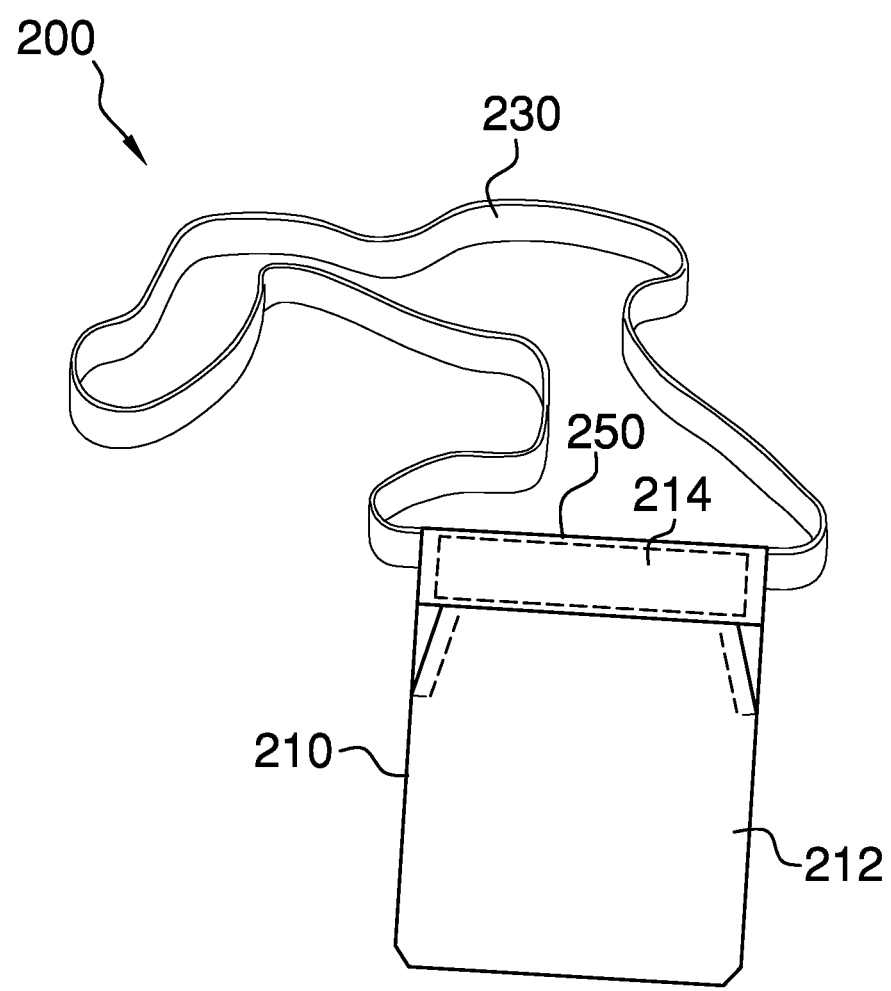
Figure 5:
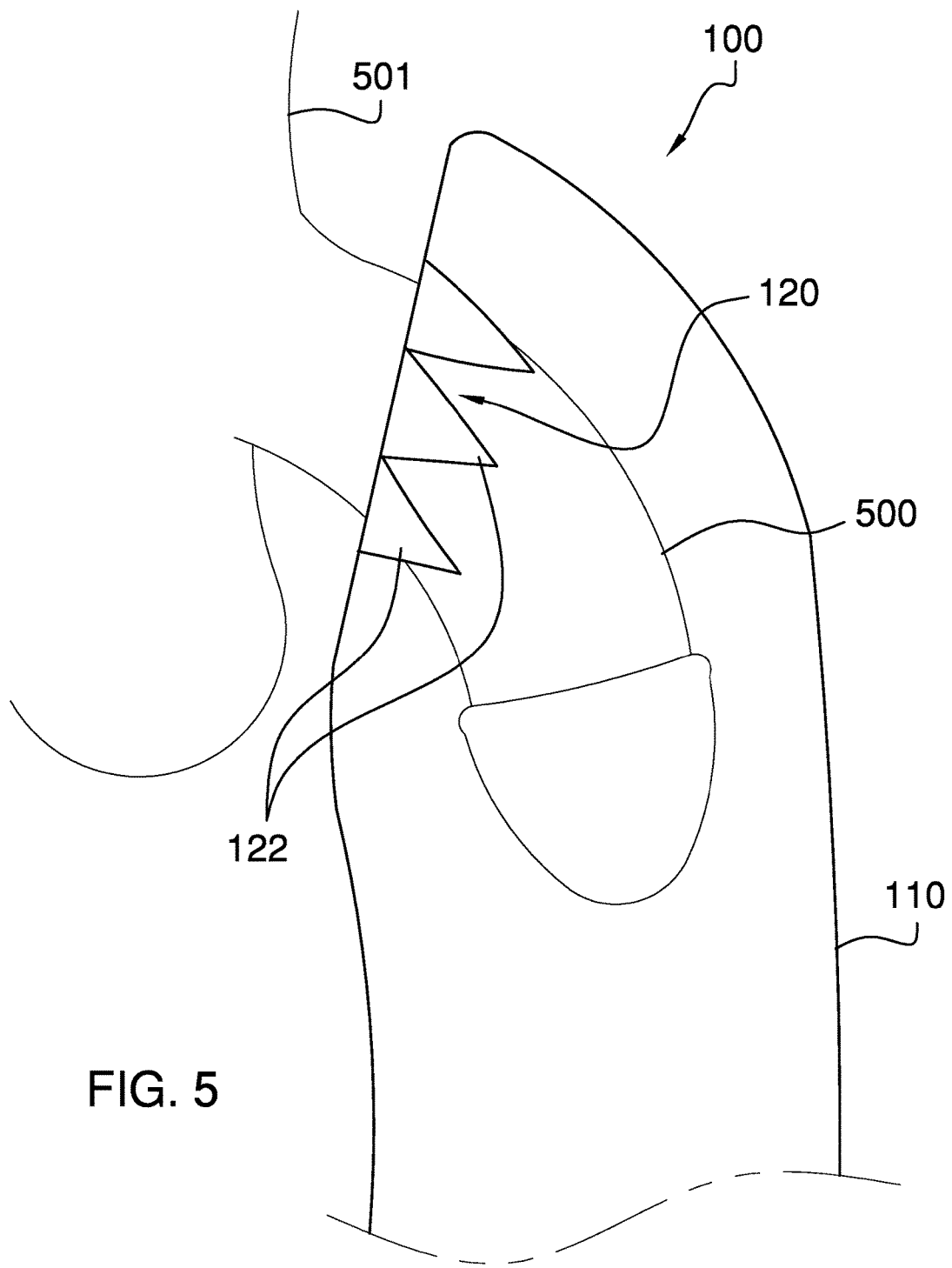
FIG. 5 is a view of an embodiment of the disclosure in use.

FIGS. 4A and 4B illustrate another example implementation of a male incontinence device 200 of the present disclosure. In some implementations, the male incontinence device 200 is similar to the male incontinence device 100 as discussed above but the body-side layer 214 of the pouch 210 may include a flap 250 configured to fold over and secure to the garment-side layer 212 (see, e.g., FIGS. 4A and 4B). In some implementations, the waistband 230 may be secured underneath the flap 250 of the pouch 210 (see, e.g., FIG. 4B). In this way, the pouch 210 may be secured to the waistband 230 of the male incontinence device 200.

As shown in FIG. 4A, in some implementations, the flap 250 may be an extension of the body-side layer 214. In some implementations, the flap 250 may include a fastener 252a thereon. In some implementations, the fastener 252a of the flap 250 may be configured to secure to a fastener 252b positioned on the exterior side of the garment-side layer 212 (see, e.g., FIG. 4A). In some implementations, the fasteners 252a, 252b may be hook-and-loop fasteners (e.g., Velcro) (see, e.g., FIG. 4A). In some implementations, the flap 250 may be secured to the exterior side of garment-side layer 212 through the use of an adhesive, snaps, buttons, magnets and/or other reclosable fasteners or any other attachment or fastening technology existing or developed in the future to secure the flap 250 to the exterior side of garment-side layer 212.

As shown in FIG. 4A, in some implementations, the first end 232a and the second end 232b of the waistband 203 may be secured together through the use of hook-and-loop fasteners (e.g., Velcro).

To secure the male incontinence device 200 in place, in some implementations, the first end 232a of the waistband 230 may be pulled around the waist of the wearer and secured to the second end 232b of the waistband. Then, in some implementations, the penis of a wearer may be inserted through the opening in the body-side layer 214 of the pouch 210. Next, in some implementations, the flap 250 of the pouch may be pushed underneath the waistband 230 (see, e.g., FIG. 4A). Then, the flap 250 may be folded over the waistband 230 and secured to the exterior side of the garment-side layer 212 (see, e.g., FIG. 4B). In this way, the pouch 210 may be supported by the waistband 230.

To remove the male incontinence device 200, in some implementations, the above steps may be performed in reverse order.

Reference throughout this specification to "an embodiment" or "an implementation" or words of similar import means that a particular described feature, structure, or characteristic is included in at least one embodiment of the present invention. Thus, the phrase "in an embodiment" or an implementation" or a phrase of similar import in various places throughout this specification does not necessarily refer to the same embodiment.

Many modifications and other embodiments of the inventions set forth herein will come to mind to one skilled in the art to which these inventions pertain having the benefit of the teachings presented in the foregoing descriptions and the associated drawings.

The described features, structures, or characteristics may be combined in any suitable manner in one or more embodiments. In the above description, numerous specific details are provided for a thorough understanding of embodiments of the invention. One skilled in the relevant are will recognize, however, that embodiments of the invention can be practiced without one or more of the specific details, or with other methods, components, materials, etc. In other instances, well-known structures, materials, or operations may not be shown or described in detail.

The inventor claims:

1. A male incontinence device comprising:
    an absorbent pouch comprising a garment-side layer and a body-side layer connected together to form an interior cavity therebetween;
    wherein the garment-side layer and body-side layer are at least connected together on a bottom side, a first side, and a second side thereof, the interior cavity of the pouch may be accessed through an opening extending through the body-side layer of the pouch that is configured to receive the penis of a wearer and an opening through a top side of the pouch; and
    a waistband coupled to the pouch, the waistband comprising a first end and a second end configured to be secured together through the use of a fastener;
    wherein the opening of the body-side layer is an aperture formed from a plurality of radial slits cut to form a plurality of flaps, the plurality of flaps are configured to fold into the interior cavity of the pouch during use;
    a first opening and a second opening that each extend through both the garment-side layer and the body-side layer of the pouch, wherein the first opening and the second opening are positioned adjacent to the top side of the pouch; and
    the first end of the waistband extends through the first opening of the pouch and the second end of the waistband extends through the second opening of the pouch.

2. The male incontinence device of claim 1 wherein the body-side layer includes a flap extending from a top side thereof, the flap is configured to fold over the waistband and secure to the garment-side layer of the pouch.

3. The male incontinence device of claim 1 wherein the pouch is comprised of a single piece of material folded back onto itself having a first end and a second end, the first end is the garment-side layer and the second end is the body-side layer.

4. The male incontinence device of claim 3 further comprises of a perimeter seal joining at least a first side edge of the garment-side layer to a first side edge of the body-side layer and a second side edge of the garment-side layer to a second side edge of the body-side layer thereby sealing the first side and the second of the pouch.

5. The male incontinence device of claim 4 further comprising a perimeter seal joining a top side edge of the garment-side layer to a top side edge of the body-side layer thereby sealing closed the opening through the top side.

6. The male incontinence device of claim 4 wherein the opening of the body-side layer is an aperture formed from a plurality of radial slits cut to form a plurality of flaps, the plurality of flaps are configured to fold into the interior cavity of the pouch during use.

7. The male incontinence device of claim 4 further comprising;
    a first opening and a second opening that extend through both the garment-side layer and the body-side layer of the pouch, wherein the first opening and the second opening are positioned adjacent to the top side of the pouch; and
    the first end of the waistband extends through the first opening of the pouch and the second end of the waistband extends through the second opening of the pouch.

8. The male incontinence device of claim 7 wherein the first opening positioned adjacent the first side of the pouch and the second opening is positioned adjacent to the second side of the pouch, the first opening and the second opening being spaced apart so as to allow access to the cavity of the pouch through the top side opening thereof.

\* \* \* \* \*